United States Patent [19]

Dionne et al.

[11] Patent Number: 5,786,216
[45] Date of Patent: Jul. 28, 1998

[54] INNER-SUPPORTED, BIOCOMPATIBLE CELL CAPSULES

[75] Inventors: Keith E. Dionne, Rehoboth, Mass.; Orion D. Hegre, Green Valley, Ariz.; Thomas R. Flanagan, Barrington; Tyrone F. Hazlett, Coventry, both of R.I.; Edward J. Doherty, Mansfield, Mass.

[73] Assignee: Cytotherapeutics, Inc.

[21] Appl. No.: 337,555

[22] Filed: Nov. 10, 1994

Related U.S. Application Data

[63] Continuation-in-part of Ser. No. 176,119, Dec. 30, 1993, abandoned, which is a continuation-in-part of Ser. No. 997,770, Dec. 24, 1992, Pat. No. 5,418,154, which is a continuation-in-part of Ser. No. 722,852, Jun. 28, 1991, abandoned, which is a continuation-in-part of Ser. No. 638,759, Jan. 8, 1991, Pat. No. 5,283,187, which is a continuation-in-part of Ser. No. 461,999, Jan. 8, 1990, Pat. No. 5,158,881, which is a continuation-in-part of Ser. No. 121,626, Nov. 17, 1987, Pat. No. 4,892,538.

[51] Int. Cl.$^6$ ............................ C12N 5/00; C12N 11/04; A61K 9/52; A61K 9/50
[52] U.S. Cl. ..................... 435/402; 424/422; 424/93.7; 435/182; 435/395; 435/400; 435/401; 604/890.1
[58] Field of Search ......................... 435/174, 177, 435/180, 182, 288, 240.22, 240.23, 240.242, 395, 400, 401, 402; 424/93.7, 422; 604/890.1, 891.1

[56] References Cited

U.S. PATENT DOCUMENTS

| | | | |
|---|---|---|---|
| 4,479,796 | 10/1984 | Kallok | 604/93 |
| 4,505,767 | 3/1985 | Quin | 148/402 |
| 4,565,589 | 1/1986 | Harrison | 148/402 |
| 4,892,538 | 1/1990 | Aebischer et al. | 604/891.1 |
| 4,941,874 | 7/1990 | Sandow et al. | 604/60 |
| 5,418,154 | 5/1995 | Aebischer et al. | 435/182 |

FOREIGN PATENT DOCUMENTS

| | | |
|---|---|---|
| WO 87/03802 | 7/1987 | WIPO. |
| WO 88/10103 | 12/1988 | WIPO. |
| WO 90/15637 | 12/1990 | WIPO. |
| WO 91/00119 | 1/1991 | WIPO. |
| WO 92/19195 | 11/1992 | WIPO. |
| WO 93/00063 | 1/1993 | WIPO. |
| WO 93/00128 | 1/1993 | WIPO. |
| WO 93/03901 | 3/1993 | WIPO. |
| WO 93/21902 | 11/1993 | WIPO. |

OTHER PUBLICATIONS

DuPont Company, "ELVAX® Resin Grades" (Product Literature), (DuPont Company Polymer Products, Wilmington, DE (Oct. 1989).

Shirai and Hayaski, "Development of Polymeric Shape Memory Material," 184, *Mitsubishi Technical Bulletin*, pp. 1–6 (Dec. 1988).

*Primary Examiner*—David M. Naff
*Attorney, Agent, or Firm*—Ivor R. Elrifi; Mintz, Levin, Cohn, Ferris, Glovsky and Popeo, P.C.

[57] ABSTRACT

A biocompatible capsule for containing cells for implantation is prepared containing an inner support that provides tensile strength to the capsule. The capsule may be a tubular semipermeable membrane such as a hollow fiber membrane having both ends sealed. A rod shaped inner support extends through the lumen and ends of the rod are attached to sealed ends of the fiber. Prior to sealing one fiber end, cells are introduced into the lumen. Cells within the capsule may be suspended in a liquid medium or immobilized in a hydrogel or extracellular matrix material, and biologically active molecules can be delivered from the capsule to surroundings or from the surroundings into the capsule. The inner support may have external features such as flutes or a roughened or irregularly-shaped surface, and may be coated with cell-adhesive substance or a cell-viability-enhancing substance. The inner support may be a hollow tube having two channels, one communicating with a filling port that permits injecting cells through the support into the capsule and the other communicating with another port that allows gas to escape through the support as cells are introduced. Anti-inflammatory agents can be incorporated into the capsule membrane to reduce immune response, and angiogenic factors and cell growth factors may be used to stimulate cell culture. Post-coating of capsule can be used to provide a protective barrier against immunogens. A tether for capsule retrieval can be formed integral with the inner support.

13 Claims, 11 Drawing Sheets

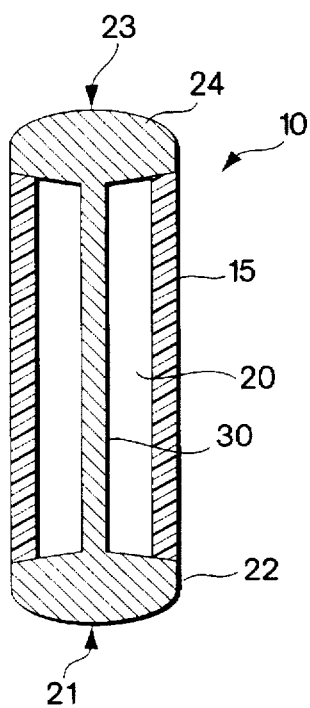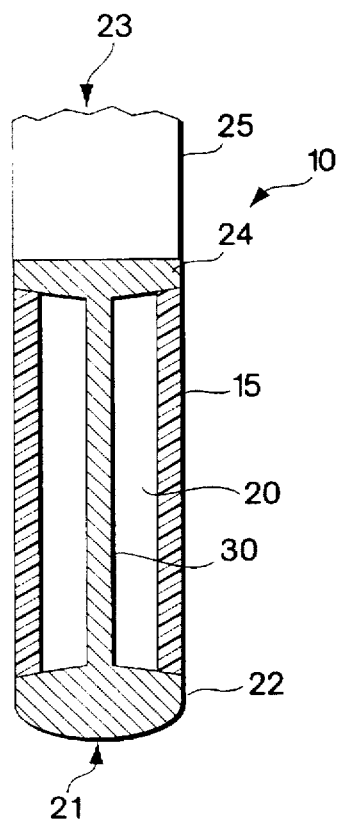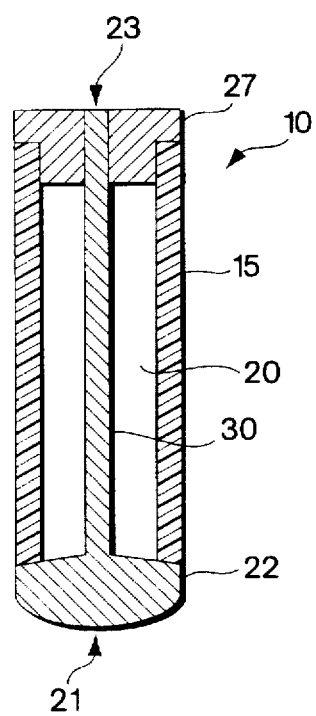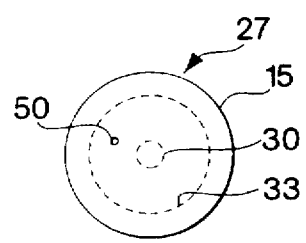
Fig. 1A
Fig. 1B
Fig. 1C
Fig. 1D

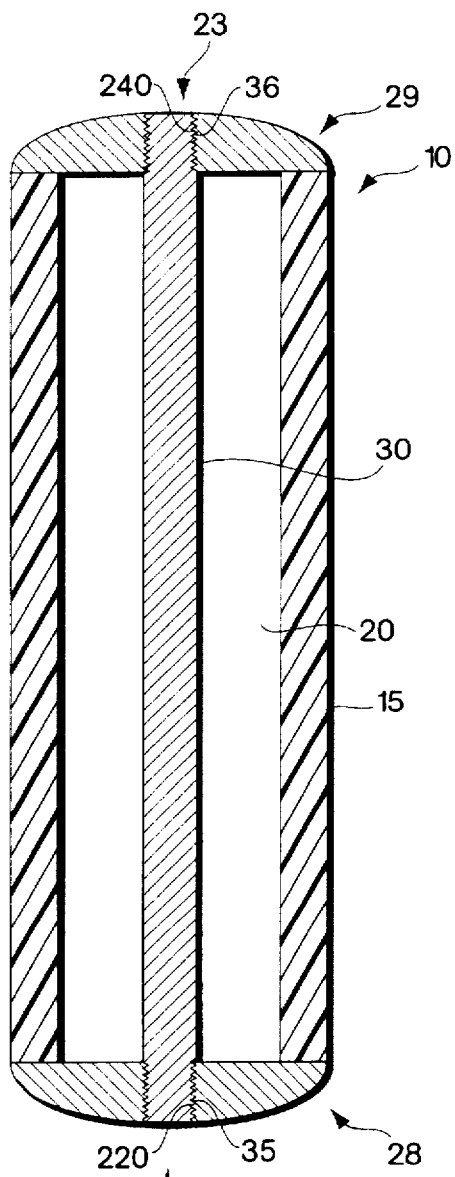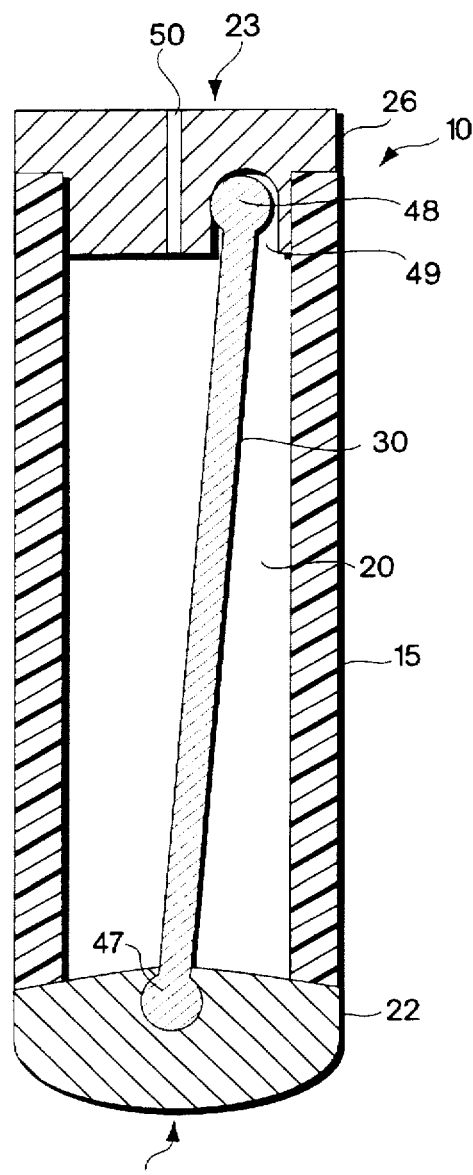

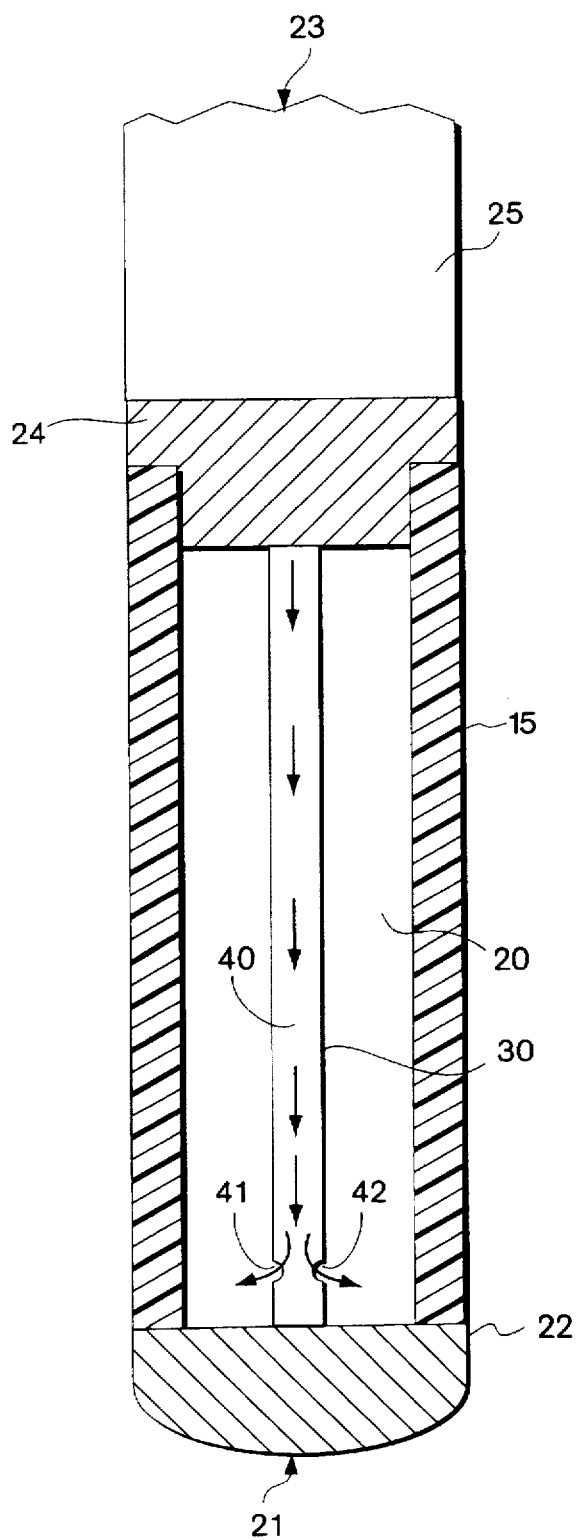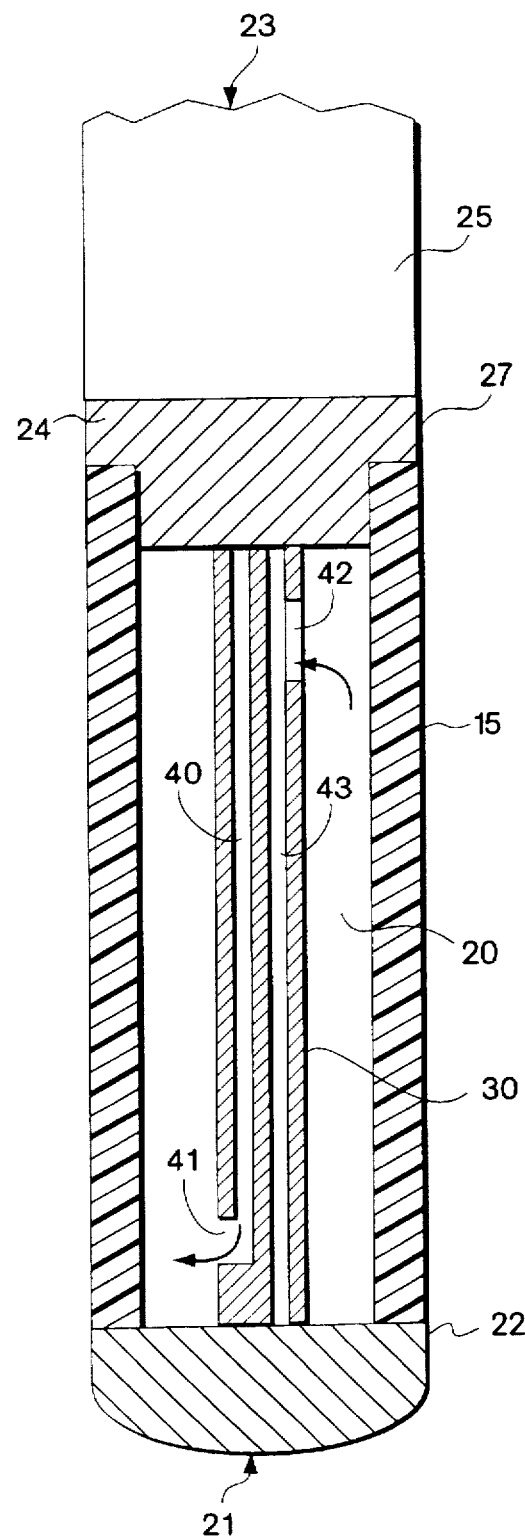
Fig. 4A
Fig. 5

INNER-SUPPORTED, BIOCOMPATIBLE CELL CAPSULES

CROSS REFERENCE TO RELATED APPLICATIONS

This application is a continuation-in-part of application Ser. No. 08/176,119, filed Dec. 30, 1993, now abandoned, which is a continuation-in-part of application Ser. No. 07/997,770, filed Dec. 24, 1992, now U.S. Pat. No. 5,418,154, which is a continuation-in-part of application Ser. No. 07/722,852, filed Jun. 28, 1991, now abandoned, which is a continuation-in-part of application Ser. No. 07/638,759, filed Jan. 8, 1991, now U.S. Pat. No. 5,283,187, which is a continuation-in-part of application Ser. No. 07/461,999, filed Jan. 8, 1990, now U.S. Pat. No. 5,158,881, which is a continuation-in-part of application Ser. No. 07/121,626, filed Nov. 17, 1987, now U.S. Pat. No. 4,892,538.

BACKGROUND OF THE INVENTION

This invention relates to cell capsules for the treatment of diseases and disorders with encapsulated cells or substances such as neurotransmitters, neuromodulators, hormones, trophic factors, growth factors, or other biologically active molecules. In particular, the invention relates to inner-supported, biocompatible cell capsules.

Many diseases or disorders, particularly neurological disorders, appear to be based, in whole or in part, on the absence or limited availability of such biologically active molecules.

For example, paralysis agitans, more commonly known as Parkinson's disease, is characterized by a lack of the neurotransmitter dopamine within the striatum of the brain, secondary to the destruction of the dopamine secreting cells of the substantia nigra.

The direct administration of purified or synthetic dopamine, its precursors, analogs, and inhibitors have been studied for therapeutic value in the treatment of Parkinson's disease. These studies have revealed various problems with delivery, stability, dosage, and cytotoxicity of the applied compounds. To date, none of these approaches has demonstrated more than marginal therapeutic value. Brain-derived growth factor also may have potential value in the treatment of Parkinson's disease because it has been demonstrated to maintain the viability of striatal neurons in vitro.

Striatal implantation of polymer rods which release sustained amounts of dopamine has been reported to alleviate experimental Parkinsonism in rodents. This indicates that the release of dopamine alone in the proper target structure may correct this functional deficiency.

Similarly, diabetes is a disease characterized by the degeneration of the pancreatic endocrine system with a resulting loss in the body's ability to produce insulin. Although diabetes can be controlled, to an extent, by daily injections of insulin, optimal treatment protocols must take into account the individual's disease state as well as daily changes in a subject's metabolism. For these reasons, polymeric matrix delivery systems for insulin have not been particularly successful.

Many other diseases are characterized by a deficiency in a critical biologically active molecule that cannot easily be supplemented by injections or longer-term, controlled release therapies. Still other diseases, while not characterized by substance deficiencies, can be treated with biologically active moieties normally made and secreted by cells. Thus, trophic and growth factors may be used to prevent neurodegenerative conditions such as Huntington's and Alzheimer's diseases, and adrenal chromaffin cells which secrete catecholamines and enkephalins have been used to treat pain.

The implantation of living cells capable of constitutively producing and secreting neurologically active factors has been attempted. Remedial transplantation of neurotransmitter-secreting tissue has been accomplished using the patient's own tissue so as not to elicit an immune response. For example, dopamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people.

Other transplantation approaches have demonstrated that even though the brain is considered "immuno-privileged", rejection ultimately occurs with both xenografts and allografts. This problem necessitates the co-administration of immuno-suppressors. Their use renders their own set of complications and deleterious side-effects.

One encapsulation approach has been macroencapsulation which typically involves loading cells into hollow fibers and then sealing the extremities. The encapsulation of such cells by a selectively permeable membrane permits diffusion of the biological factor yet restrains the cells within a specific location. Encapsulation may also reduce or prevent host rejection in the case of xenogeneic (cross-species) or allogeneic transplantation. However, the macrocapsules in the prior art are somewhat flexible and susceptible to bending and kinking. Further, some of the prior art macrocapsules have been prone to damage upon removal from the host.

Various types of cell capsules are known. Aebischer-I (U.S. Pat. No. 4,892,538) discloses a selectively permeable hollow fiber membrane for cell encapsulation. The cell-containing hollow fibers of Aebischer-I may be sealed permanently with caps or glue, or may be sealed reversibly with removable, friction-fitted caps. Aebischer-I's Example I uses tubes having an internal diameter of 600 microns and a jacket thickness of 100 microns. Aebischer-II (U.S. Pat. No. 5,158,881) discloses a method for encapsulating viable cells by forming a tubular extrudate around a cell suspension and sealing the tubular extrudate at intervals to define separate cell compartments joined by polymeric links. Dionne et al. (WO 92/19195) discloses a biocompatible immunoisolatory vehicle. Mandel et al. (WO 91/00119) discloses a selectively permeable cell closeable membrane tube for implantation in a subject having a large pore hydrophobic outer surface to encourage vascularization. Aebischer-III (WO 93/00128) discloses a renewable implant having a U-tube shaped membrane with an external center for aid in insertion.

During the insertion process, the capsules may be subject to compression stresses. Typical insertion schemes include delivery of the capsule to the treatment site via a cannula. It is desirable that the capsule be delivered to the site intact so that the cells are retained in the capsule. Once in place, such capsules may be subject to additional stresses which can cause bending and kinking of the relatively fragile capsule walls. Capsules implanted in the peritoneum, for example, may exhibit such behavior. It is desirable to have a capsule of improved strength to withstand stresses both during insertion and upon implantation at the target site.

In most instances, it is desirable that such capsules be readily retrieved. In some cases, for example, the therapy may have a defined end point (i.e. delivery of growth hormone). The implanted cells may also become oncogenic or tumor-forming. A dose adjustment may require a reduction in the number of implanted cells at specific times. It is therefore desirable to have a capsule with improved tensile strength and which may be reliably and completely retrievable. Some of the prior art capsules are not easily retrievable as they are prone to breakage upon retrieval. During retrieval, tension is one of the primary stresses on the capsule.

Additionally, there are a variety of factors that may influence the strength of polymeric membranes used to construct macrocapsules. The type of polymer and its molecular weight are important factors. The membrane geometry, including the fiber wall thickness and the capsule dimensions, can be important. These membrane characteristics can also have effect on the function of the capsule, including the transport of small molecules into and out of the capsule. The longer the fiber, for instance, the more likely it will develop kinks or twists. Thinner fiber walls, which may be desirable for some applications, may not provide adequate fiber strength. Therefore, some additional type of support may be required.

It is desirable that a capsule not only be of sufficient strength but also biocompatible. When xenogeneic or allogeneic cells are encapsulated, it is generally also desirable that the capsule be immunoisolatory.

In some instances, encapsulated cells may form a necrotic core in the center of the capsule. Nutrients must diffuse into the capsule and waste products must be able to leave the capsule to maintain cell viability. Such a core may develop over time due to a shortage of certain metabolites reaching the center of the capsule or the buildup of toxic products which causes cells to die. In these instances, because the central area of the capsule does not support viable cells and the necrotic tissue is nonfunctional, the necrotic core may not contribute to the overall function of the implanted capsule. As dying cells accumulate and begin to break down, the necrotic tissue may also release factors which are detrimental to the surviving cells (e.g., factors which elicit a macrophage or other immune response). Additionally, the extra space in the center of the capsules may lead to slower reaction times and to potential overshoot (i.e., overproduction of a biologically active molecule) requiring more biologically active molecules (e.g., insulin or other feedback controlled substrate) to obtain an equivalent transmembrane gradient for transport of the substrate across the membrane. It may therefore be desirable to prevent or minimize the development of such a core.

Because of reduced cell necrosis with inner-supported capsules, a shorter capsule length can be used to achieve a given level of delivery of a biologically active molecule. In studies on Streptozotocin induced diabetes in rats, we have found that use of an inner support in the implanted capsules enabled a 5-fold reduction in length of the capsule from 30 cm to 6 cm using a similar cell density (approximately 7% islet/alginate).

It is further desirable to utilize capsules having increased surface area to volume ratios and reduced diffusion distances for delivery of the biologically active molecule across the selectively permeable capsule jacket.

SUMMARY OF THE INVENTION

The present invention addresses the foregoing problems by providing an inner-supported, biocompatible cell capsule that can be implanted into a recipient animal and when appropriate, easily retrieved. The capsules of the present invention have at least one selectively permeable surface across which biologically active molecules can be delivered. Delivery of such molecules can be from the capsule to the host or from the host to the capsule. The inner-supported capsules of this invention have increased surface area to volume ratios as well as smaller diffusion distances.

In one embodiment of the invention, the cell capsule is a coaxial tube assembly with a cylindrical inner support. In this embodiment, the inner support may be added as a discrete component and sealed to both ends of the cell capsule. The support may also be formed integrally with either a top or bottom sealing fitting.

In another embodiment, the inner support is provided with additional external surface characteristics. For example, the inner support may have fins extending radially along the axis of the cell capsule. Alternately, the external surface of the inner support may be roughened or irregularly-shaped.

In another embodiment, the inner support is hollow tube and may be aligned concentrically with a filling port. The inner support is provided with openings which communicate with the filling port and also with the cell chamber. In this embodiment, cells can be injected through the filling port and allowed to flow from the inner support into the cell chamber. A second port may also be provided to allow for the escape of air from the chamber as cells are introduced through the filling port.

Definitions

As used herein, "a biocompatible capsule" means that the capsule, upon implantation in a host mammal, does not elicit a detrimental host response sufficient to result in the rejection of the capsule or to render the capsule inoperable. Such inoperability may occur, for example, by formation of a fibrotic structure around the capsule limiting diffusion of nutrients to the cells therein.

As used herein, "an immunoisolatory capsule" means that the capsule upon implantation into a mammalian host minimizes the deleterious effects of the host's immune system on the cells within its core such that the capsule functions for extended periods of time in vivo.

"Biological activity" refers to the biological effects of a molecule on a specific cell. As used herein, "a biologically active molecule" is a molecule which may exert its biological activity within the cell in which it is made (e.g., bcl–2 to prevent apoptosis) or it may be expressed on the cell surface and affect the cell's interactions with other cells or biologically active molecules (e.g., a neurotransmitter receptor or cell adhesion molecule). Additionally, a biologically active molecule may be released or secreted from the cell in which it is made and exert its effect on a separate target cell (e.g., a neurotransmitter, hormone, growth factor, or cytokine).

BRIEF DESCRIPTION OF THE DRAWINGS

FIG. 1A is a cross-sectional side view of an inner-supported capsule of the present invention with the inner support connected at both ends of the capsule;

FIG. 1B is a cross-sectional side view of an inner-supported capsule of the present invention with the inner support connected at both ends of the capsule and a tether attached at one end of the capsule;

FIG. 1C is a cross-sectional side view of an inner-supported capsule of the present invention with the inner support connected at both ends of the capsule where one end of the capsule is formed by a hub seal fitting and the inner support is connected to that hub seal fitting;

FIG. 1D is a top view of an integral hub seal fitting and inner support with a filling port;

FIG. 1E is a cross-sectional side view of an inner-supported capsule of the present invention with a threaded inner support and where the ends of the capsule are formed by threaded sealing fittings and the threaded inner support is connected to those sealing fittings;

FIG. 1F is a cross-sectional side view of an inner-supported capsule of the present invention with a sealing ball attached at both ends of the inner support where the inner support is connected at one end of the capsule to slotted fitting 26 having a slot 49 adapted to receive inner support 30;

FIG. 4A is a cross-sectional side view of a capsule having a hollow inner support forming a channel, into which a cell suspension can be injected and allowed to flow into the chamber;

FIG. 5 is a cross-sectional side view of a capsule having a channeled inner support as in FIG. 4A and FIG. 4B and additionally having a second port to allow for escape of air;

Like reference characters in the respective figures indicate corresponding parts.

DETAILED DESCRIPTION

Figure 1I:
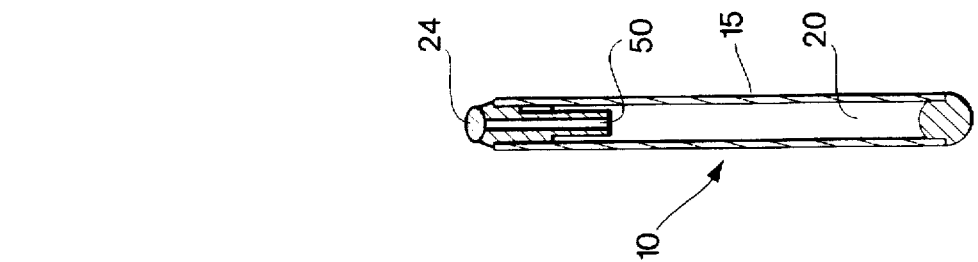
FIG. 1I is a cross-sectional side view of a sealed inner-supported capsule of the present invention with hub assembly and frangible neck portion removed.

This invention is directed to an improved inner-supported, biocompatible cell capsule. The capsule has at least one selectively permeable surface across which biologically active molecules can be delivered to the surrounding tissue. The capsule may include means for introducing cells therein following implantation.

The inner-supported capsule of the instant invention comprises (a) an inner support, (b) a core which contains a cell or cells, either suspended in a liquid medium or immobilized within a hydrogel or extracellular matrix material and (c) a surrounding or peripheral region of selectively permeable matrix or membrane (jacket) which is biocompatible. If desired, the capsule can be constructed to minimize the deleterious effects of the host's immune system on the cells in its core.

The inner support may be made from any material which is substantially non-toxic to cells of the core and which has a tensile strength greater than or equal to the tensile strength of jacket. Polymeric materials which could be used include acrylates (such as alkaline methacrylates, cyano acrylates, polymethyl acrylate and poly((2-dimethylamino) ethyl methacrylate)), urethanes, silicones, PVC, PAN/PVC, epoxies, etc. Alternatively, the inner support may be made of a metal or alloy such as medical grade titanium or stainless steel. Polymeric or metallic shape memory materials may also be used for the inner support. Such polymeric shape memory materials are known. See, e.g., Shirai and Hayashi, *Mitsubishi Technical Bulletin*, 184, pp. 1–6 (1988). Metallic shape memory materials are also known. See, e.g., U.S. Pat Nos. 4,505,767 and 4,565,589.

The core of the polymer capsule is constructed to provide a suitable local environment for the continued viability and function of the cells isolated therein. The instant capsule can be used to contain a wide variety of cells and cell lines.

Many transformed cells or cell lines are most advantageously isolated within a capsule having a liquid core. For example, cells can be isolated within a capsule whose core comprises a nutrient medium, optionally containing a liquid source of additional factors to sustain cell viability and function such as fetal bovine or equine serum.

Suitably, the core may be composed of a matrix formed by a hydrogel which stabilizes the position of the cells. The term "hydrogel" herein refers to a three-dimensional network of crosslinked hydrophilic polymers. The network is in the form of a gel, substantially composed of water, preferably but not limited to gels being greater than 90% water. Cross-linked hydrogels can also be considered solids because they do not flow or deform without appreciable applied shear stress.

Compositions which form hydrogels fall into three classes for the purposes of this application. The first class carries a net negative charge and is typified by alginate. The second class carries a net positive charge and is typified by extracellular matrix components such as collagen and laminin. Examples of commercially available extracellular matrix components include Matrigel™ and Vitrogen™. The third class is neutral and is typified by crosslinked polyethylene oxide. Alternatively, other matrices or spacers, which are not necessarily crosslinked, may also be employed within the core. Alternative matrices include precipitated chitosan, synthetic polymers and polymer blends, microcarriers and the like, depending upon the growth characteristics of the cells to be encapsulated.

The jacket of the capsule may be made of a material which is the same as that of the inner support or the core, or it may be made of a different material. In either case, the material used results in a surrounding or peripheral region which is selectively permeable and biocompatible. The jacket may also be constructed to be immunoisolatory if desired.

Various polymers and polymer blends can be used to manufacture the capsule jacket. Polymeric membranes forming the capsule may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, and PAN/PVC as well as derivatives, copolymers, and mixtures thereof.

The capsule jacket may also include a hydrophobic matrix such as an ethylene vinyl acetate copolymer, or a hydrophilic matrix such as a hydrogel. The jacket may be post-production coated or treated with an impermeable outer coating such as a polyurethane, ethylene vinyl acetate, silicon, or alginate covering part of the cell chamber.

The solvents used in conjunction with the above-identified polymers in forming the jacket will depend upon the particular polymer chosen for the membrane material. Suitable solvents include a wide variety of organic solvents such as alcohols and ketones generally as well as dimethylsulfoxide (DMSO), dimethylacetamide (DMA), and dimethylformamide (DMF) and blends of these solvents as well. In general, water-miscible organic solvents are preferred.

The polymeric solution (or "dope") can also include various additives such as surfactants to enhance the formation of porous channels and antioxidants to sequester oxides that are formed during the coagulation process. Exemplary surfactants include Triton-X 100 available from Sigma Chemical Corp. and Pluronics P65, P32, and P18. Exemplary anti-oxidants include vitamin C (ascorbic acid) and vitamin E.

In addition, anti-inflammatory agents can also be incorporated into the polymeric membrane to reduce immune response while angiogenic factors and cell growth factors may be used to stimulate cell culture. Exemplary anti-inflammatory agents include corticoids such as cortisone and ACTH, dexamethasone, cortisol, interleukin-1 and its receptors and agonists, and antibodies to TGF, interleukin-1, or γ-interferon. Exemplary angiogenic factors include fibroblast growth factor and nerve growth factor. Alternatively, these materials can be added to the capsules after manufacture or formation by a post-coating or spraying process. For example, the capsules can be immersed in a solution containing an anti-inflammatory agent, an angiogenic factor, or a growth factor.

Post-coating procedures can also be used to provide a protective barrier against immunogens and the like. For example, after formation, the cell capsule can be coated (e.g., by immersion, spraying or applying a flowing fluid during extrusion, if applicable) with a surface protecting material such as polyethylene oxide or polypropylene oxide to inhibit protein interactions with the exposed cell chambers. Other protective coatings include silicon and hydrogels such as alginates. Derivatives of these coating materials such as polyethylene oxide-polydimethyl siloxane may also be used.

The jacket may be formed freely around the core without chemical bonding, or alternatively, the jacket may be directly cross-linked to the core matrix. In either case, formation of the vehicle of the present invention does not require the presence of polymers with a charge opposite that of the core in an interfacial layer of the jacket, but they can be there.

The jacket allows passage of substances up to a predetermined size but prevents the passage of larger substances. More specifically, the surrounding or peripheral region is produced in such a manner that it has pores or voids of a predetermined range of size. As a result, the vehicle is selectively permeable. The molecular weight cutoff (MWCO) selected for a particular capsule will be determined in part by the application contemplated. Membranes useful in the instant invention are ultrafiltration and microfiltration membranes. Preferably the MWCO for ultrafiltration membranes is 150 kD or less, most preferably to 70–130 kD. Microfiltration membranes having a MWCO of greater than 130 kD retain cells within the capsule while allowing the passage of most molecular species.

Referring to FIG. 1A, one embodiment of capsule 10 comprises a standard cell chamber 20 formed by jacket 15 and glue seals 22 and 24. Distal tip 21 of the cell capsule is sealed with a bottom glue seal 22 and proximal tip 23 is sealed with a top glue seal 24 to form chamber 20.

In this embodiment, any suitable selectively permeable hollow fiber can be used to construct the inner supported capsules of this invention. For example XM-50 tubes (AMICON Corp., Lexington, Mass.) may be used. Alternately, selectively permeable hollow fiber membranes may be formed as described in U.S. Pat. Nos. 5,284,761 or 5,283,187, herein incorporated by reference.

In this embodiment, inner support 30 is inserted through the lumen of the hollow fiber. Both the sealing of the distal end 21 of the hollow fiber and the securing of inner support 30 to the distal end of the hollow fiber are performed with a polymer glue such as light cured acrylate. Inner support 30 is preferably manually centered within the bead of glue seal 22 that seals distal end 21 of the hollow fiber. The cells are then introduced into the hollow fiber through the unsealed end (the proximal end). Both the sealing of the proximal end 23 of the hollow fiber and the securing of the support 30 to the proximal end of the hollow fiber are preformed with a polymer glue, such as light cured acrylate. It should be noted that any suitable glue may be used. Inner support 30 is preferably manually centered within the bead of glue seal 24 that seals proximal end 23 of the hollow fiber. As the capsule is formed, an excess of inner support may protrude from the distal and/or proximal ends. The excess is removed after the capsule is formed. Such a sealing method is referred to in, e.g., U.S. Pat. 4,892,538, herein incorporated by reference. In the sealed inner supported capsule of this embodiment an inner support 30 extends between and is connected to capsule ends by glue seals 22 and 24. Inner support 30 reinforces the cell capsule and preferably resides in the center of the cell chamber.

Alternatively, the capsule ends may be sealed to the inner support by crimping, knotting, heat sealing, screwing, or any other suitable method. In the case of heat-sealed capsules, seals may be formed by melting the jacket 15 and allowing it to solidify around and attach to the inner support. Glue may be injected to facilitate seal formation. Such suitable sealing techniques, including the employment of polymer adhesives and/or crimping, knotting and heat sealing, are known in the art. See, e.g., J. Altman et al., "Successful Pancreatic Xenografts Using Semipermeable Membrane", 5 *Artificial Organs* (Suppl.) 776 (1981) (Polyvinylchloride acrylic XM50 copolymer tubing biocompatible epoxy or cyacrylate glue); J. Altman et al., "Long-Term Plasma Glucose Normalization in Experimental Diabetic Rats With Macroencapsulated Implants of Benign Human Insulinomas", 35 *Diabetes* 625, (1986) (poly(acrylonitrile-co-vinyl-chloride) (PAN/PVC) copolymer glue in solvent);

B. Dupuy et al., "In Situ Polymerization of membranes around cells); W. Hymer et al., "Pituitary Hollow Fiber Units In Vivo and In Vitro", 32 *Neuroendocrinology* 33 9 (1981) (PAN/PVC fibers syringe loaded, crimping with heated forceps); H. Iwata et al., "The Use of Photocrosslinkable Polyvinyl Alcohol in the Immunoisolation of Pancreatic Islets", 22 *Transplant Proceedings* 797 (April 1990) (Production of encapsulated cells using photocrosslinkable hydrogel); Y. Kojima et al., "Xenogeneic Pancreatic Islet Transplantation Using a Millipore Diffusion Chamber", 19 *Transplant Proceedings* 981 (February 1987) (Millipore MF cement); P. Lamberton et al., "Use of Semipermeable Polyurethane Hollow Fibers for Pituitary Organ Culture", 24 In vitro *Cellular & Developmental Biology* 500 (June 1988); C. Lum et al., "Intraperitoneal Nucleopore Chambers: a Murine Model for Allograft Rejection", 20 *Transplant Proceedings* 173 (April 1988) (Nucleopore membranes attached with silicone sealant; Millipore MF cement); S. Ronel et al., "Macroporous Hydrogel Membranes for a Hybrid Artificial Pancreas", 17 *J. Biomed. Materials Res.* 855 (1983) (Pressure/heat sealing of hydrogel cell capsules); N. Theodorou et al., "Problems in the Use of Polycarbonate Diffusion Chambers for Syngeneic Pancreatic Islet Transplantation in Rats", 18 *Diabetologia* 313 (1980) (Polycarbonate filters sealed with polyacrylic cement); F. Wong et al., "Effects of Thymus Enclosed in Millipore Diffusion Envelopes on Thymectomized Hamsters", 28 *Blood* 40 (1966); and G. Zondervan et al., "Design of a Polyurethane Membrane for the Encapsulation of Islets of Langerhans", 13 *Biomaterials* 136 (1992) (Polyurethane tubing sealed by knotting).

In addition, any suitable "dry" sealing method can also be used. The membrane materials used in the cell capsules have a tendency to hold water in the pores of the membrane upon exposure to aqueous solutions, such as cell media. Sealing a membrane which has been exposed to such solutions can be problematic. In dry sealing methods, a substantially nonporous fitting is provided through which the cell-containing solution is introduced. Subsequent to filling, the capsule is sealed.

The term "dry" seal is defined as a seal formed between a substantially moisture or water-free jacket and the fitting. The absence of moisture or water in the pores of the jacket, caused by contact with the solution, substantially reduces seal failure, e.g., precipitation of the adhesives employed. Further, the absence of cell solution elements, such as proteins, decreases contamination of the adhesive so that it may effectively bond between the opposing adhesive sites' surfaces.

Preferable adhesives for "dry" sealing, are substantially rapidly polymerizing adhesives, such that potential toxic contamination of the cells by uncured adhesive is reduced. Additionally, the adhesive must not discharge sufficient toxic by-products to be substantially detrimental to cell viability. Hence, the adhesive must also substantially polymerize completely. Suitable adhesives include light-curable acrylate polymer adhesive, two-part polyurethane adhesives, epoxies, silicones, and other acrylate polymers.

If the cell solution contacts the opposing adhesive sites' surface, the solution can be easily removed in a suitable manner. For instance, a volatile, biocompatible solvent may be applied on a swab to wipe the fitting surfaces so that the surfaces become "dry" or free of contaminates.

Referring to FIG. 1B, the embodiment of FIG. 1A is shown with a tether 25 attached to top glue seal 24. The tether 25 can be post-coated with a material (e.g., a polyurethane or the like) which imparts additional strength to the tether. The tether may be formed as a discrete component, in which case it is affixed to the capsule by gluing, heat sealing, friction fitting, or any other suitable securing means. Alternatively, the tether is formed integrally with either the capsule jacket or the inner support. Such tethered cell capsules can find a variety of applications, particularly when implanted in a subject for delivery of active factors. In use, the cell capsule can be located as close to the target region, or treatment site, (e.g., in the brain, peritoneal cavity or elsewhere) as desired while the other end of the tether can be fixed at a convenient anchor point or disposal in a readily accessible location for retrieval.

Referring to FIG. 1C, another embodiment of capsule 10 comprises a standard cell chamber 20 formed by jacket 15, glue seal 22, and a hub seal fitting 27. The inner support may be connected to the hub seal fitting 27 by a glue seal or any other suitable means (including friction fitting or mechanical attachment). Alternately, the inner support and the hub seal fitting may be fabricated integrally. The hub seal fitting may be integral with or attached to a tether 25.

In cases where the support 30 and the hub seal fitting 27 are integral, the hub seal may also contain a port 50 for introducing cells. See FIG. 1D as an illustration. In such cases, the capsule 10 may be preassembled, having one end completely sealed. The hub seal fitted with an inner support is then attached to the opposite end. Cells are then introduced in the chamber 20 through port 50. The port is then sealed. The jacket has an inner wall 33.

Referring to FIG. 1E, where the capsule 10 is fabricated step-wise, the support 30 may be added as a discrete component, linking threaded seal fittings 28 and 29. In such an embodiment, inner support 30 is provided with male threads 35 and 36 on each end. Both the bottom threaded sealing fitting 28 and top threaded sealing fitting 29 are provided with female threads 220 and 240 which mate with the threads on threaded inner support 30. A threaded sealing fitting 28 is sealed to the jacket 15 at the distal end 21, preferably using an acrylate glue. Support 30 is then inserted into chamber 20 and male thread 35 threaded and sealed into female thread 220 of bottom sealing fitting 28, preferably also with light cured acrylate. Next, cells are added to the chamber 20 and male thread 36 is threaded and sealed into female thread 240, again preferably with acrylate glue of the top threaded sealing fitting 29. The top threaded sealing fitting 29 is then sealed to the proximal end 30 of the jacket, also preferably using a light cured acrylate.

Alternatively, as illustrated in FIG. 1F, inner support 30 is provided with sealing balls 47 and 48 on each end. The slotted fitting 26 is provided with a slot 49 for receiving the inner support 30 and a port 50 for receiving the cells. The proximal end 23 of the hollow fiber is sealed to a slotted fitting 26. Both the securing of distal end 21 of the hollow fiber and the securing of inner support 30 to the distal end of the hollow fiber are performed with a polymer glue such as light cured acrylate. Resultantly, the distal end 21 of the hollow fiber is sealed to the inner support with a glue seal 22. Next, cells are added to the chamber 20 via port 50 and then port 50 is sealed.

Figure 1H:
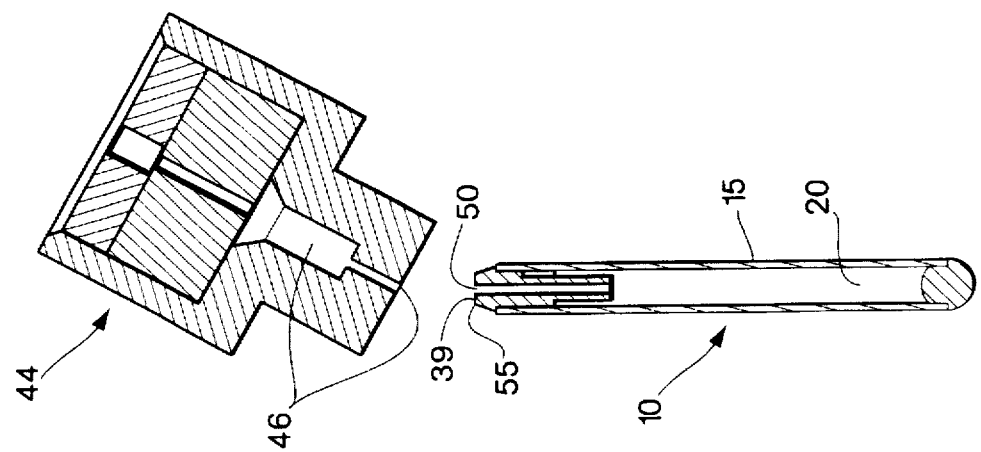
FIG. 1H is a cross-sectional side view of an inner-supported capsule of the present invention with a hub assembly and frangible neck portion removed after breaking.
Figure 1G:
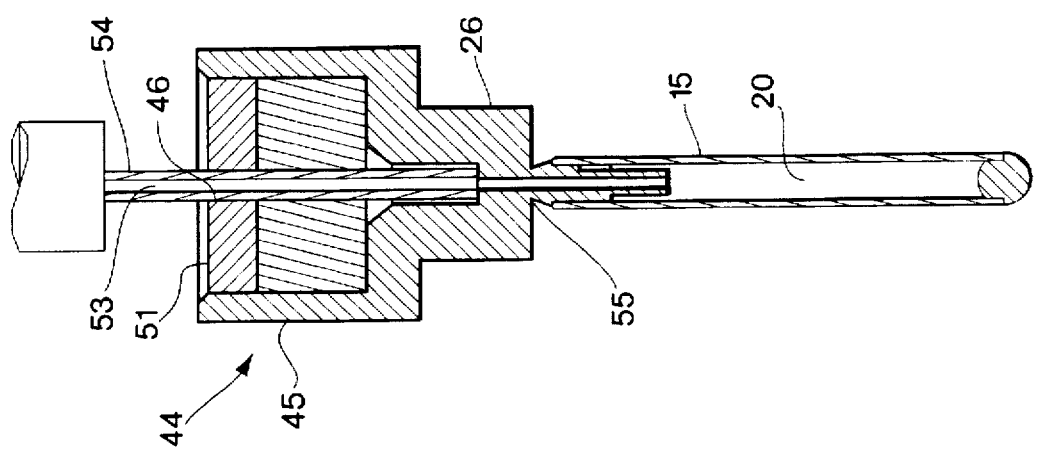
FIG. 1G is a cross-sectional side view of an inner-supported capsule at the present invention with a hub assembly and frangible neck portion attached.
Figure 1J:
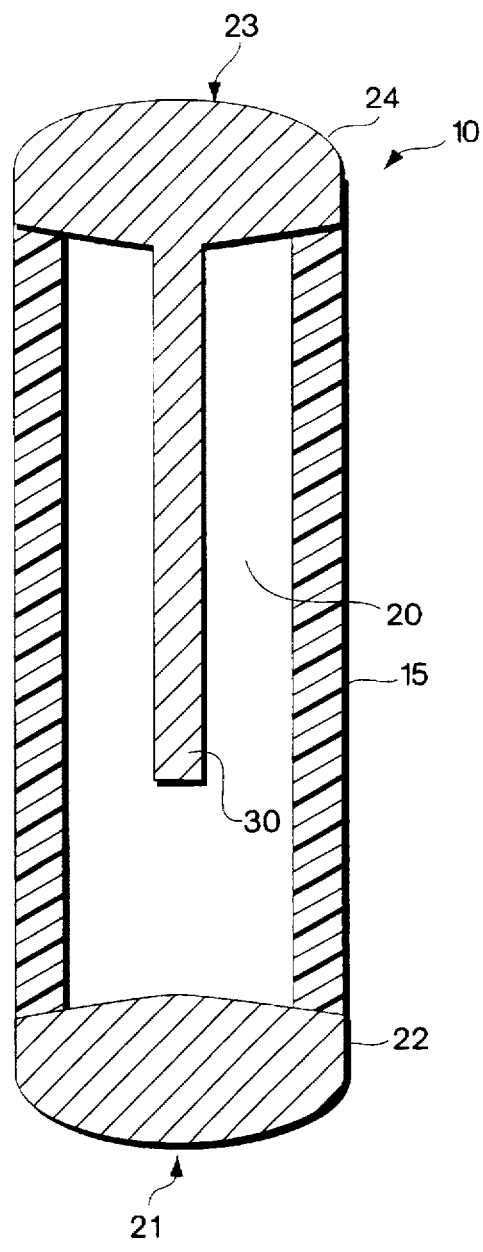
FIG. 1J is a cross-sectional side view of an inner-supported capsule of the present invention with the inner support connected at only one end of the capsule.
Figure 1K:
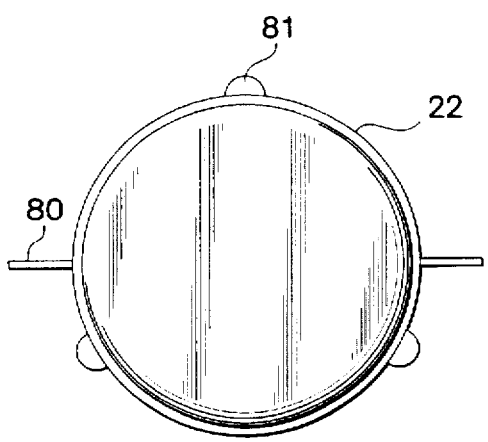
FIG. 1K is a top view of a flat sheet inner-supported capsule.
Figure 1L:
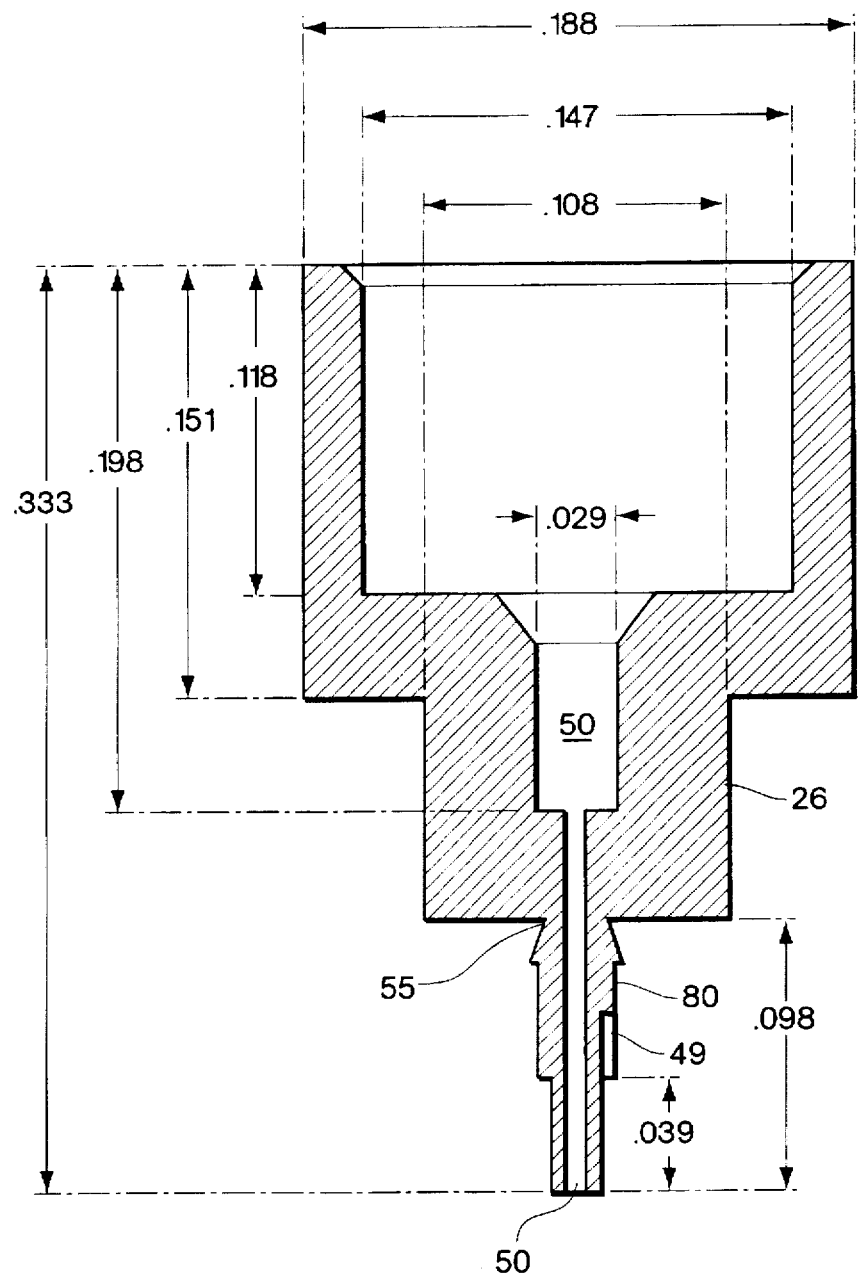
FIG. 1L is a cross-sectional side view of the slotted fitting 26 of FIG. 1F, indicating a slot 49 adapted to receive an inner support 30.

In a preferred embodiment illustrated in FIGS. 1F and 1L, the slotted fitting 26 comprises an annular fitting including an access port 50 extending through the fitting. More particularly, the annular fitting includes a leg portion 80 (FIG. 1L) which is insertable into the lumen of the hollow fiber. The leg portion 80 is connected to a base portion of the annular fitting so that upon insertion of the leg portion, the proximal end of the hollow fiber seats against the bottom of the base portion of the fitting. The leg portion of the fitting has an outer rim further shaped to provide a slot 49 adapted to receive the inner support. Thus, when installed in this hollow fiber embodiment, the inner support is oriented substantially along the length of the fiber, but is slightly off center with respect to the access port. Access to the central filling port 50 is thus unaffected by the position of the inner support.

The annular fitting is preferably substantially rigid and may be composed of one of a number of suitable biocompatible materials which are substantially non-toxic to the living cells. These materials include polyurethanes, epoxies, silicones, and acrylate polymers like alkaline methacrylates, cyano acrylates, polymethyl methacrylate and poly((2-dimethylamino)ethyl methacrylate.

A substantially rapidly polymerizing adhesive is used to provide the "dry-seal" between the leg 80 of the slotted fitting 26 and the inner wall of the hollow fiber membrane.

Referring to FIG. 1F, and FIG. 1L, the inner support 30 may be formed integrally with a slotted fitting 26. In such an embodiment, the inner support and the slotted fitting are first secured to jacket 15 at the proximal end. The distal end of the capsule is then sealed with a glue seal (or an alternative sealing technique) such that the seal is also attached to the inner support 30. Next, cells are added to the chamber 20 via port 50 and then port 50 is sealed. Alternatively, inner support 30 may be integrally formed with seal 21 at the distal end of the capsule. Fitting 26 is then secured to the proximal end of the capsule such that inner support 30 is received in fitting 26.

As illustrated in FIGS. 1G–1I, one preferred embodiment of the present invention includes a detachable necked hub assembly 44 coupled to base 37 of the annular fitting by a frangible neck portion 55. Note that FIGS. 1G–1I, being illustrative only of a detachable or frangible necked hub fitting, do not indicate a slot for the inner support. It will be appreciated that such a slot can be fabricated into the leg portion as shown in FIGS. 1F and 1L. Hub assembly 44 is capable of selective separation from the fitting upon breaking of the frangible neck portion 55 at a frangible region thereof.

Hub assembly 44 includes a housing 45 which provides a passageway 46 positioned in axial alignment with open bore 50 of annular fitting 26. Hence, while annular fitting 26 is "dry" sealed to jacket 15, the lumen may be accessed through passageway 46 and open bore 50.

Passageway 46 includes a cavity portion 53 formed and dimensioned to receive and seat a seal member 54 therein. Seal member 54 provides an access hole extending therethrough, in coaxial alignment with passageway 46 to permit deposition of cell solution into chamber 20. A cap member 51 is provided to be positioned over seal member 54 which is snap fit or snugly engaged to retain the cap member in place.

Housing 45 may be integrally formed with annular fitting 26 and may be fabricated using conventional machining or molding techniques. This housing may be composed of an acrylate polymer or the like.

Seal member 54 is preferably composed of a resilient flexible material such as silicone. The resiliency of seal member 54 creates a seal sufficient to prevent contaminants from entering chamber 20 during filling thereof.

Subsequently, cell suspension may be filled, injected or deposited into chamber 20.

When the capsule is filled with cell solution, the necked hub assembly may be selectably and manually separated from annular fitting 26. Upon breaking the frangible neck portion 55 and separating the hub assembly 44, a virgin bonding surface 39 and the end of open bore 50 is exposed which subsequently must be sealed.

Exposed open bore 50 of the annular fitting may be closed or sealed using a light curable acrylate adhesive (e.g., Luxtrak™ LCM adhesives, Ablestick Adhesives, Zeneca Inc., Wilmington Del.) or other biocompatible adhesive to form glue seal 24 to seal the open bore. In the light curable glue approach, a blue light may be employed which is not damaging to the viability of the cells.

As illustrated in the embodiment of FIG. 1J, inner support 30 may be connected to only one end of the capsule by a glue seal 24 (or, an alternative sealing technique). In this embodiment, the support is preferably rigid and will serve a space-filling function and may also serve as a reservoir for a substance that enhances cell viability. Inner support 30 will help prevent kinking in capsules constructed according to this embodiment.

Various methods for forming selectively permeable hollow fiber membranes are known in the art. In one method, hollow fibers are formed by coextrusion of a polymeric casting solution and a coagulant (which can include biological tissue fragments, organelles, or suspensions of cells and/or other therapeutic agents). Such a method is referred to in U.S. Pat. Nos. 5,284,761 or 5,283,187, herein incorporated by reference.

Following extrusion, the polymeric solution preferably forms a selectively permeable membrane upon coagulation. The membrane is a porous structure. The permeability of the polymeric membrane can be varied by controlling the viscosity of the polymeric casting solution such that upon coagulation, the coating will form with a network of microchannels to provide diffusion pathways. In one embodiment, this can be achieved by employing a water-miscible solvent as a component of the polymeric solution and maintaining a pressure differential between the coagulant and the polymeric solution during extrusion. As the tubular extrudate forms, water from the coagulant infiltrates into the coagulating polymer to replace the solvent as the solvent is driven outward by the pressure difference. Upon coagulation, the water which has infiltrated into the polymeric membrane provides a network of pores. The optimal pressure and viscosity varies with the solvent and polymer employed but can readily be ascertained for any particular polymer/solvent combination by those skilled in the art without undue experimentation.

It will be appreciated that the inner support may have a variety of shapes. The shape of the inner support may be dictated in part by the shape of the capsule.

For tubular (or "hollow fiber") embodiments, the inner support may form a cylindrical tube or rod, a rectangular tube or rod, or any other oblique shape, so as long as it can fit within the lumen of the hollow fiber. It will be appreciated that in some embodiments, the inner support may have fins or other protrusions which may contact the inner wall of the hollow fiber. In such embodiments, separate cell compartments within the capsule may be formed.

Figure 2:
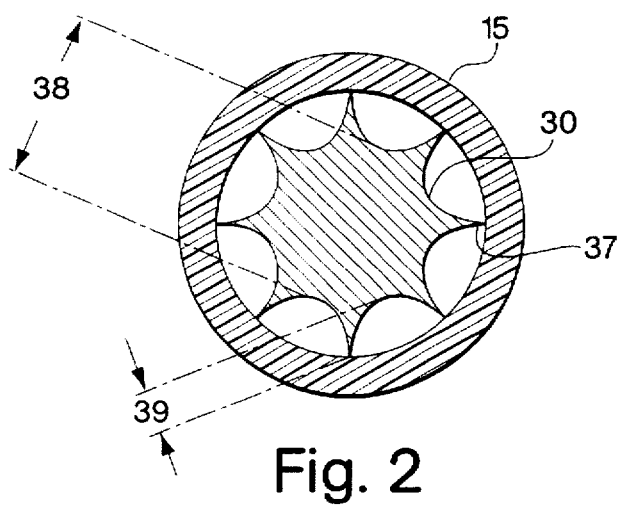
FIG. 2 is a top cross-sectional view of a finned inner support.

In another embodiment, as illustrated in FIG. 2, the external surface of the inner support 30 is finned. The fins of the inner support 30 extend radially along the axis of the capsule 10. Such a design increases the surface area of the inner support which may be beneficial to some cell types. In the embodiment shown in FIG. 2, the inner support diameter is the sum of the length of the inner support central rod (measured by 38) and twice the length of a fin 37 (measured by 39).

Figure 3:
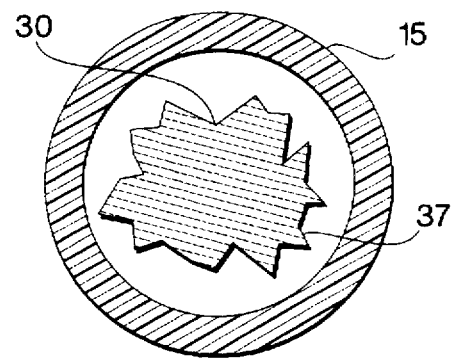
FIG. 3 is a top cross-sectional view of roughened or irregularly-shaped inner support.

In an alternate embodiment, shown in FIG. 3, the external surface of the finned inner support 30 may be roughened. This feature may help keep cells distributed throughout the unoccluded lumen space.

When used in a hollow fiber embodiment the inner support may widen or flare at one or both ends, e.g., as shown in FIG. 1F, to facilitate adhesion to the glue seal or other fitting at the capsule ends. The widening may be in the shape of a ball, or other suitable geometry that increases the surface area of ends of the inner support available for securing the inner support to the capsule seals or fittings. Such a widening of the ends of the inner support also provides increased mechanical support to secure the inner support to the capsule ends.

Figure 4B:
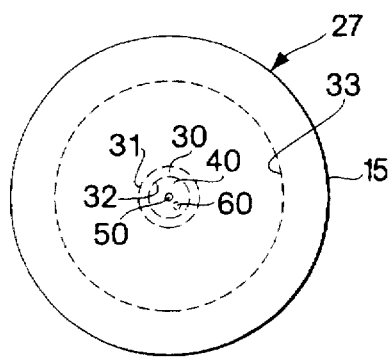
FIG. 4B is a top view of an integral hub seal fitting with a filling port and hollow inner support forming a channel, into which a cell suspension can be injected and allowed to flow into the chamber.

In a further embodiment, as illustrated in FIG. 4A and FIG. 4B, the inner support 30 may be hollow defining a channel 40. The inner support 30 has an outer support wall 31 and an inner support wall 32. The channel 40 may be aligned concentrically with a filling port 50 provided through the tether 25 and the top fitting 24. The inner support 30 has openings 41 and 42 which communicate with channel 40 and the interior of the chamber 20. In such a configuration, cells can be injected through port 50 and allowed to flow from channel 40 into chamber 20. In capsules containing such a hollow support 30, substances such as growth or trophic factors which help sustain the cells, may be inserted into the channel 40 after the cells have been introduced into the chamber 20. A second port 60 may also be provided through tether 25 and top fitting 24 to allow for the escape of air from chamber 20 as cells are introduced through port 50 and channel 40.

Figure 6:
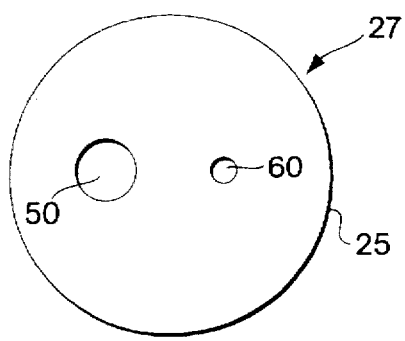
FIG. 6 is a top cross-sectional view of the inner support of FIG. 5.

Another embodiment in which the inner support tube 30 is hollow is illustrated in FIGS. 5 and 6. Inner support tube 30 defines two channels 40 and 43. Cells can be injected through port 50 and allowed to flow from channel 40 into the chamber 20. The walls of support 30 may be permeable, and the support 30 may be continuous with a reservoir containing substances which are known to enhance cell viability such as perfluorocarbons.

Substances which help sustain the cells may be inserted into the chamber 20 through port 50 provided through tether 25 and hub seal fitting 27 and then through channel 40 after the cells have been introduced into the chamber 20. A second port 60 is also provided through tether 25 and hub seal fitting 27 and aligns with channel 43 of support 30 to allow for the escape of air from chamber 20.

It will be appreciated that the inner-supported capsules of the present invention may have a variety of shapes.

The capsule may use hollow fibers for encapsulation or may be in the form of a flat sheet capsule. FIG. 1K illustrates a flat sheet capsule, having a first flat sheet membrane with a first interior surface, and a second flat sheet membrane with a second interior surface, mounted to engaging perimeter surfaces of a scrim, wire mesh, or other appropriate support material positioned between the membranes such that the membranes are spaced-apart from each other, the interior surfaces of the membranes are oriented to face each other, and the membranes and support define a chamber. The support may be formed with an inner surface defining one or more access ports extending through the fitting. Cells may then be introduced through the access port, and the seal completed with a plug inserted into the port.

When tether 25 is to be used as an aid in fixing and retrieving the capsule 10, it may be desirable to have the inner support 30 integral to tether 25. This eliminates the additional step of attaching tether 25 to the capsule 10. Additionally, since these capsules are generally loaded through a cannula system, it is desirable to use as small a diameter cannula as practicable to minimize tissue damage to the recipient. Forming inner support 30 integral with tether 25 eliminates the need to slip tether 25 over the hub seal fitting 27 or the glue seal 24 for attachment thereby reducing the overall diameter of capsule 10. A seamless juncture between inner support 30 and tether 25 will also improve overall strength of the capsule 10.

The inner-supported capsules of the present invention provide improved strength against compression stress which is the primary type of stress that occurs during insertion of the capsule. The capsule may also undergo some tensile stress and some shear stress as well as some bending during and after implantation.

One primary stress encountered by the capsule 10 during retrieval is tension. As the inner support 30 is formed integrally with the hub seal fitting 27 of the capsule 10 and is formed of a material which has a tensile strength at least equal to the tensile strength of jacket 15, inner support 30 in the various embodiments will be used to bear much of the load instead of the jacket 15.

Inner-supported capsules will have both increased surface-to-volume ratios as well as smaller diffusion distances.

A wide variety of cells may be used in this invention. These include well known, publicly available immortalized cell lines as well as dividing primary cell cultures. Examples of publicly available cell lines suitable for the practice of this invention include baby hamster kidney (BHK), chinese hamster ovary (CHO), mouse fibroblast (L-M), NIH Swiss mouse embryo (NIH/3T3), African green monkey cell lines (including COS-a, COS-7, BSC-1, BSC-40, BMT-10 and Vero), rat adrenal pheochromocytoma (PC12), rat glial tumor (C6), RIN cells, β-TC cells, Hep-G2 cells, and AT T20 cells. Primary cells that may be used according to the present invention include bFGF-responsive neural progenitor-stem cells derived from the CNS of mammals (Richards et al., *PNAS* 89, 8591–8595 (1992); Ray et al., *PNAS* 90, 3602–3606 (1993)), primary fibroblasts, Schwan cells, astrocytes, oligodendrocytes and their precursors, myoblasts, adrenal chromaffin cells, and the like.

The choice of cell depends upon the intended application. The encapsulated cells may be chosen for secretion of a neurotransmitter. Neurotransmitters are small molecules (less than 1,000 daltons molecular weight) which act as chemical means of communication between neurons. Such neurotransmitters include dopamine, gamma aminobutyric acid (GABA), serotonin, acetylcholine, noradrenaline, epinephrine, glutamic acid, and other peptide neurotransmitters. Cells can also be employed which synthesize and secrete agonists, analogs, derivatives or fragments of neurotransmitters which are active, including, for example, cells which secrete bromocriptine (a dopamine agonist) and cells which secrete L-dopa (a dopamine precursor).

The encapsulated cells can also be chosen for their secretion of hormones, cytokines, growth factors, trophic factors, angiogenesis factors, antibodies, blood coagulation factors, lymphokines, enzymes, analgesics and other therapeutic agents or agonists, precursors, active analogs, or active fragments thereof. These include enkephalins, catecholamines (e.g., norepinephrine and epinephrine), endorphins, dynorphin, insulin, factor VIII, erythropoietin, Substance P, nerve growth factor (NGF), Glial-derived Neurotrophic Factor (GDNF), platelet-derived growth factor (PDGF), epidermal growth factor (EGF), brain-derived neurotrophic factor (BDNF), neurotrophin-3 (NT-3), an array of fibroblast growth factors, and ciliary neurotrophic factor.

Alternatively, one or more biologically active molecules may be delivered into the capsule. For example, the capsule may contain one or more cells or substances which "scavenge" cholesterol, or other biologically active molecules from the host.

In some aspects of the invention, the cell is allogeneic (i.e., cells from another of the same species as the subject in which it is to be implanted), autologous or syngeneic (from the same individual), or xenogeneic (i.e., cells from another of a different species).

The recipient may be any suitable animal, preferably a mammal, most preferably a human.

It may also be desirable to encapsulate multiple cell types within a capsule. In one instance, a first type of cell may have an augmentary effect on substance secreting cells of a second type after the method of Aebischer-IV (U.S. Pat. No. 5,182,111). In another instance, it may be desirable to coencapsulate two or more cell types which may both secrete a desired biologically active substance.

In order that this invention may be better understood, the following examples are set forth. These examples are for purposes of illustration only and are not to be construed as limiting the scope of this invention in any manner.

EXAMPLES

Example 1—Strength Test

The tensile and compression strength of an inner-supported capsule was compared with that of a non-supported capsule.

Capsules without an inner support were constructed using a double-skinned selectively permeable membrane. The selectively permeable membrane was cast, according to the methods described in U.S. Pat. No. 5,284,761 (herein incorporated by reference), from a dope of 12½% (w/w) PAN/PVC in DMSO. The resultant hollow fiber had a typical outside diameter of 900 microns and an inside diameter of 750 microns. The MWCO was 70 kD. The hollow fiber was sealed at both ends (without infusion of any cells) with a silicon sealant (Dow Corning, MI). The capsule length was 5 cm.

Inner-supported capsules were constructed using similarly made hollow fibers. Inner-supported capsules of the same length were made by inserting a solid polyurethane inner support (Thermedics, Woburn, Mass.) having an outside diameter of 500 microns into a hollow fiber such that an excess of inner support protruded from the distal end of the fiber and the proximal end of the fiber. The hollow fiber was sealed at both the distal end and the proximal end with silicon sealant, securing the inner support approximately centrally therein. The excess portion of the inner support protruding from each end was then cut away. No cells were added.

Strength measurements were performed on a Vitrodyne™ strength testing system, having V2000™ software (Vitrodyne, Inc., VT).

As shown in Table I, the (tensile) yield point of the capsule is approximately 1.5±0.2 mPa, the (tensile) break point is approximately 2.0±0.2 mPa, the % (tensile) elongation is 55±3, and the (compression) yield point is 1.0±0.4 mPa. However, in a capsule containing a polyurethane inner support (500 µm outside diameter), the (tensile) yield point ranged between approximately 5.3 and 7.5 mPA, the (tensile) break point ranged between approximately 7.1 and 10.5 mPA, the % (tensile) elongation ranged between approximately 50 and 55, and the (compression) yield point was approximately 2.2±0.6 mPa.

TABLE I

Tensile and Compression Data for Empty Fibers and Inner-supported Fibers

| Fiber Type | Tensile | | | Compression |
|---|---|---|---|---|
| | Yield Point (mPa) | Break Point (mpa) | % Elongation | Yield Point (mPA) |
| PAIN fiber only (n = 6) | 1.5 ± 0.2 | 2.0 ± 0.2 | 55 ± 3 | 1.0 ± 0.4 |
| PAIN fiber with support (n = 3) | 5.3,7.5,7.5 | 7.1,9.5,10.5 | 50/55/52 | 2.2 ± 0.6 |

There is a 350–500% increase in tensile strength with the inner support in place. The fiber elongation was basically held constant—however, the energy required to reach that elongation increased considerably.

If an increase in strength of more than 500% is required, this can be achieved by changing the durometer of the polyurethane or by using different materials for the inner support 30.

There is also an improvement in compression strength of the capsule when an inner support 30 is used. This indicates that there is less of a chance of damaging the jacket 15 during the insertion process.

Example 2—Durability Test

The durability of inner-supported capsules were compared with that of non-supported capsules.

Both sets of test capsules were prepared using the double skinned PAN/PVC hollow fiber membranes formed by a wet dry jet spinning technique, substantially as described in Example 1. These hollow fibers had a 3 mm inside diameter and were too weak to be self-supporting (e.g., the membrane tube would collapse if drained of water and would kink if segments longer than 1 cm were held at one end and held in open air).

Two types of inner supports were used: (1) finned silicone rods of 85 shore A durometer, having a central 2 mm rod with four 0.5 mm fins at 90° angles (Specialty Silicone, Paso Robles, Calif.) (3.0 mm total diameter), and (2) silicone tubing (Specialty Silicone, Paso Robles, Calif.) (2.5 mm outside diameter) with a commercially available stainless steel wire inserted through the center of the tubing.

The inner supports were inserted into the lumen of the PAN/PVC hollow fibers such that an excess of support protruded from the distal end and proximal end of the fiber. After insertion, the shell region between the support and the membrane was filled with 1% alginate (Kelco), which was crosslinked by immersion for 6 minutes in 1% $CaCl_2$ solution. The ends of the capsules were sealed by dipping the fiber ends in a solution of 85% DMSO/15% water for 15 seconds, wicking off the excess solvent, injecting polymer glue (12% PAN/PVC in DMSO) and heating the ends by touching them for 2 seconds with a sterile forceps heated to 250° F. The excess inner support was either melted and solidified to the jacket or cut away.

Inner-supported capsules ranged in length from 6 cm to 16 cm. The capsules were implanted in the peritoneal cavity of a normal dog for 18 days. Normally, after a couple of days, non-inner-supported fibers of this length and this strength would be ripped in several places, completely folded over on each other and enmeshed in a ball of fibrous tissue.

After 18 days, the inner-supported fibers were removed and found to be completely intact. No rips or major folds were found. The extent of trauma was limited to small kinks and wrinkles along the fiber. No macroscopic damage was observed to any of the peritoneal organs upon removal of the fibers.

Example 3—Retrieval Test

The increase in strength imparted to the capsules by the use of an inner support was also evaluated using a retrieval test.

Nine prior art capsules (three each of three types of selectively permeable fiber) and nine inner-supported capsules (three each of three types of selectively permeable fiber) were placed in liquid gelatin at ambient temperature. HF42293-2 represents a Type 1, single skinned fiber CP11-93-008 represents a Type 2, single skinned fiber. CP11-93-011 represents a Type 4, double skinned fiber Such Type 1, Type 2 and Type 4 fibers are described, e.g., in Lacy et al., *Science*, 254, pp. 1782–84 (1991), Dionne et al., (WO 92/19195) and U.S. Pat. No. 5,284,761. The hollow fibers used in this Example were produced substantially as described in Example 1.

The capsules were 5 cm in length. The inner supports were cylindrical and had an outside diameter of 500 microns. The outside diameter of the capsule was 900 microns and inner diameter was 750 microns. The capsules were sealed at both ends with a silicon sealant (Dow Corning, MI). The capsules were made by inserting the polyurethane inner support into a hollow fiber such that an excess of inner support protruded from both the distal end of the fiber and the proximal end of the fiber. The hollow fiber was sealed at the distal end and proximal end with the silicon sealant securing the inner support centrally therein. The excess inner support was then removed. No cells were added.

Each capsule was placed at a depth of approximately 4 cm into the gelatin, with approximately 1 cm remaining outside the gelatin. The gelatin had been prepared at twice the normal concentration. After the capsules were placed in the liquid gelatin, the gelatin was then refrigerated for approximately four hours. The outer pores of the capsules were penetrated by the liquid gelatin prior to cooling. This was done in order to simulate some form of tissue ingrowth which may happen in vivo.

Each of the non-inner-supported capsules was then removed from the gelatin using forceps. Four of the nine non-inner-supported capsules broke. One of these capsules broke 1 cm from the end placed within the gelatin, two broke 2 cm from the end placed within the gelatin, and one broke 3 cm from the end placed within the gelatin.

Each of the inner-supported capsules was removed from the gelatin by hand using the exposed part of the inner support. None of the inner-supported capsules broke upon retrieval. The data is shown in Table II.

TABLE II

| Sample | Supported/ Unsupported | Break/ No-Break | Location of Break |
|---|---|---|---|
| Type 1 HF42293-2 | Unsupported | Break | =2 cm from end within the Jell-O |
| Type 1 HF42293-2 | Unsupported | Break | =3 cm from end within the Jell-O |
| Type 1 HF42293-2 | Unsupported | No-Break | |
| Type 1 HF42293-2 | Supported | No-Break | |
| Type 1 HF42293-2 | Supported | No-Break | |
| Type 1 HF42293-2 | Supported | No-Break | |
| Type 2 CP11-93-008 | Unsupported | Break | =1 cm from end within the Jell-O |
| Type 2 CP11-93-008 | Unsupported | Break | =2 cm from end within the Jell-O |
| Type 2 CP11-93-008 | Unsupported | No-Break | |
| Type 2 CP11-93-008 | Supported | No-Break | |
| Type 2 CP11-93-008 | Supported | No-Break | |
| Type 2 CP11-93-008 | Supported | No-Break | |
| Type 4 CP11-93-0011 | Unsupported | No-Break | |
| Type 4 CP11-93-0011 | Unsupported | No-Break | |
| Type 4 CP11-93-0011 | Unsupported | No-Break | |
| Type 4 CP11-93-0011 | Supported | No-Break | |
| Type 4 CP11-93-0011 | Supported | No-Break | |
| Type 4 CP11-93-0011 | Supported | No-Break | |

Example 4—Increased Surface Area To Volume Ratio

The following calculations demonstrate that inner-supported capsules have a higher surface area to volume ratio than comparable capsules without an inner support.

Figure 7A:
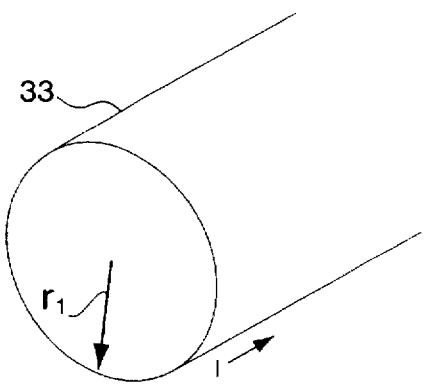
FIG. 7A is a side perspective view of a non-inner-supported capsule.

As illustrated in FIG. 7A, given a known volume of tissue $V_t$, a fixed capsule length, l, and an inner radius $r_1$ for a capsule with no inner support, the following equations hold:

$$V_{t1} = \pi r_1^2 l;$$

$$S = 2\pi r_1 l; \text{ and}$$

$$S/V_{t1} = 2/r_1$$

Figure 7B:
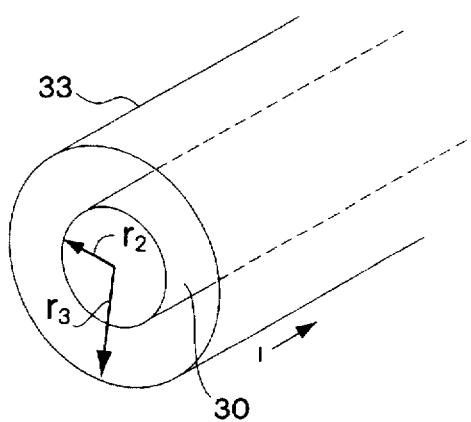
FIG. 7B is a side perspective view of an inner-supported cell capsule.

By comparison for the capsule 10 illustrated in FIG. 7B, which has an inner radius $r_3$ for the capsule and with a radius $r_2$ for the outside radius of the inner support 30, the following equations hold:

$$V_{t2} = \pi(r_3 - r_2)^2 l;$$

$$S = 2\pi r_3 l; \text{ and}$$

$$S/V_{t2} = 2r_3/(r_3 - r_2)^2$$

If $r_1 = r_3$, and $r_2$ is greater than zero, the surface area to volume ratio ($S/V_{t2}$) for the inner-supported capsule of FIG. 7B will always be greater than the surface area to volume ratio ($S/V_{t1}$) for the non-inner-supported capsule of FIG. 7A. If, for example, $r_1 = 250$ μm and $r_2 = 125$ μm, then $S/V_{t2} = (1.56)S/V_{t1}$.

Where $r_1=r_2$, and $V_{f1}=V_{f2}$, $r_3=1.44r_2$. This means that if $r_1$ is 250 µm (providing a 500 µm inside diameter), the equivalent volume inner-supported capsule has $r_3=360$ µm (for an inside diameter of 720 µm), with an increase in S/V of 1.44.

Example 5—Reduced Diffusion Distance

The following demonstrates that inner-supported capsules have a diffusion distance less than that of comparable capsules without an inner support.

Cells loaded in the capsule of FIG. 7A will have a maximum diffusion distance of 250 µm. In the capsule illustrated in FIG. 7B cells will have a maximum diffusion distance of 110 µm. Therefore, the maximum diffusion distance for the inner-supported capsule of FIG. 7B is less than half the maximum diffusion distance of the capsule of FIG. 7A.

Note that the loading density is higher in the capsule without an inner support. For example, using the capsule dimensions given above (i.e., where $r_1=r_2$), loading the equivalent number of cells in a capsule without an inner support results in a 3-fold increase in tissue loading density compared to the same capsule with an inner support. However, the S/V ratio of the inner-supported capsule is increased by a factor of 1.56 and the overall maximum diffusion distance is decreased by a factor of 2.

Example 6—Lewis Rat Test

Three cm long, finned silicon inner supports, having a central 2 mm rod with four 0.5 mm fins at 90° angles (Specialty Silicone, Paso Robles, Calif.) (3 mm total diameter) were inserted into the fiber of 3 mm inside diameter, double skinned PAN/PVC membranes to form inner-supported transplantation chambers, as described in Example 2.

Rat islet aggregates (ICA's) were prepared by collagenase isolation of rat islets, Ficoll™ purification and controlled trypsinization of purified islets. Cell clusters ranging from approximately 1–100 cells were obtained and cultured overnight. These ICAs were suspended in 1% sodium alginate (Kelco) and injected into the shell space between the inner support and the PAN/PVC membrane. After injection, the alginate was crosslinked by immersion of the capsule into 1% $CaCl_2$ for 6 minutes. The ends of the capsules were sealed with PAN/PVC, as described in Example 2.

Alternatively, one end of PAN/PVC membrane was sealed as described in Example 2. Then, islet/alginate slurry was injected so as to fill ½ of the fiber volume starting at the sealed end, and the polyurethane supports made by sealing both ends of 1.5 mm outside diameter polyurethane tubing inserted into the center of the open end of the fiber so as to displace the alginate/islet slurry pushing it into the space between the inner support and the surrounding membrane. The alginate was then crosslinked using $CaCl_2$ and the remaining open end of the capsule was then sealed as described in Example 2.

The capsules were implanted IP into male Lewis rats which had been made diabetic by the injection of Streptozotocin such that their non-fasting blood glucose levels were greater than or equal to 400 mg/dl. Animals received, on average, 2000 islet equivalents (150 µm diameter islet) (this is a minimal dosage) encapsulated in 2 capsules totaling 6 cm in length.

The animals were monitored for weight loss, blood glucose and urinary glucose. Animals showed improvement in blood glucose, decrease in urinary glucose and ketones, and gained weight. Despite the use of the large diameter capsule, none of the animals became hypoglycemic during the course of the experiment, whereas in the absence of an inner support, hypoglycemia was often seen in mice with capsules larger than approximately 1.5 mm inside diameter.

Example 7—Perfusion Test

Rat islet cell aggregates were prepared as in example 6 (approximately 7% density $Ca^{++}$ crosslinked alginate) and were loaded in one of three configurations: (1) 3 mm inside diameter fiber (as described in example 2) without an inner support; (2) 3 mm inside diameter fiber with a silicone finned inner support, having a central 2 mm rod with four 0.5 mm fins at 90° angles (3.0 mm total diameter); and (3) 3 mm inside diameter fiber with a silicone finned inner support, having a central 2 mm rod with four 0.5 mm fins at 90° angles (3.0 mm total diameter) and with the PAN/PVC membrane then being removed, leaving a crosslinked alginate/ICA mixture surrounding the inner support.

The inner supported capsules were prepared, infused with cells, and sealed as described in Example 2.

The three capsule configurations were then placed in separate chambers in a perfusion system wherein they were perfused with media (MEM) initially containing 100 mg/dl glucose at a flow rate of 0.5 ml/min. Media was collected in a fraction collector for later insulin and glucose assay by RIA and glucose oxidase respectively.

Figure 8A:
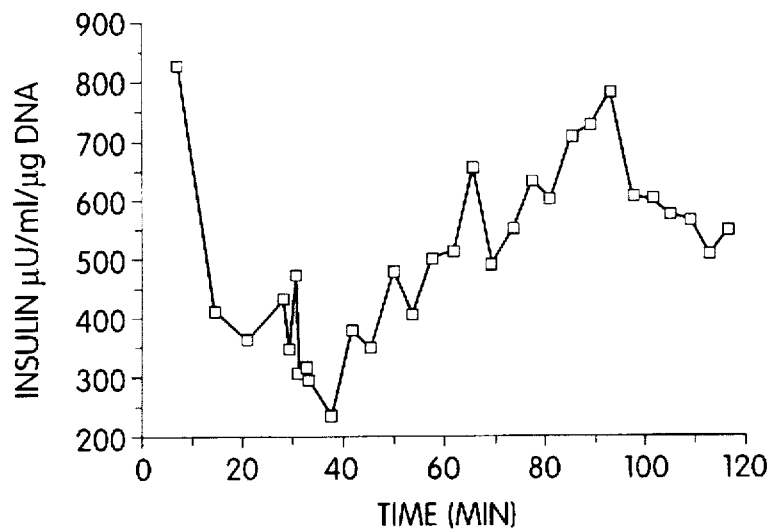
FIGS. 8A–8D are graphs in which insulin production by rat islet cell aggregates (ICAs) is plotted as a function of time. Results are shown for: ICAs in capsules without an inner support (FIG. 8A); ICAs in capsules with an inner support (FIGS. 8B, 8C); and for controls having an alginate core and an inner support but no selectively permeable capsule jacket (FIG. 8D).
Figure 8B:
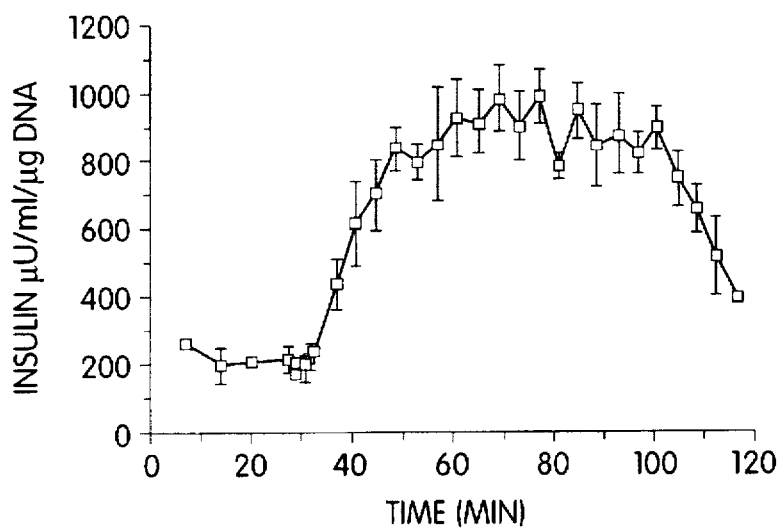
Figure 8C:
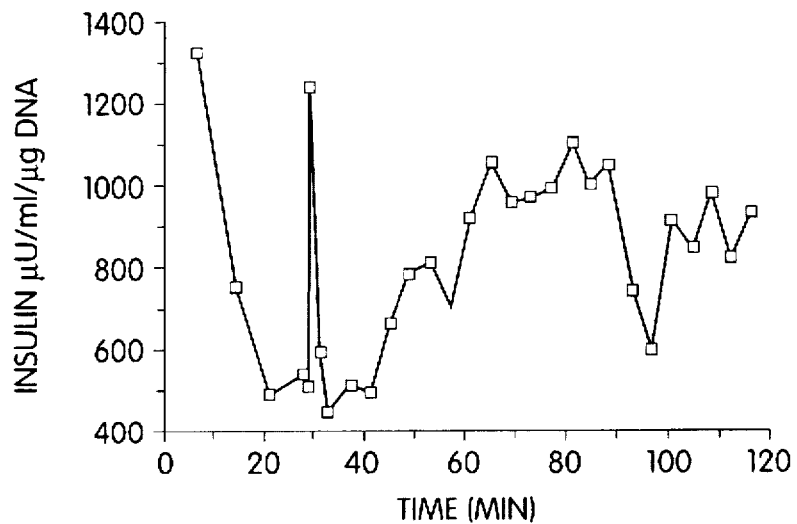
Figure 8D:
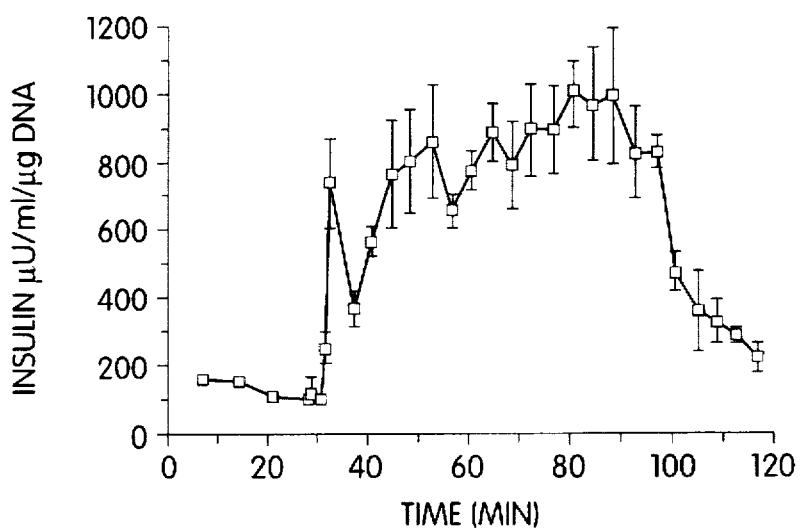

After an initial period of basal perfusion, the media was changed to one containing 300 mg/dl glucose for 40 minutes at which time media was switched back to 100 mg/dl. Insulin release from the configurations was measured as a function of time and is shown in FIGS. 8A, 8B, 8C and 8D. FIG. 8A is for configuration (1). FIGS. 8B and 8C are for configuration (2). FIGS. 8D is for configuration (3).

Configuration (1) (FIG. 8A), without the inner support, displayed a very slow insulin response to the change in perfusate glucose concentration—presumably due to the large diffusion distances with their resulting gradients and to the large internal sink for insulin build-up. Both configurations (2) (FIGS. 8B and 8C) and (3) (FIG. 8D) showed more rapid response to upward and downward changes in perfusate glucose concentration, with little differences between the two configurations.

Example 8—Stress-Deflection Test

Figure 9:
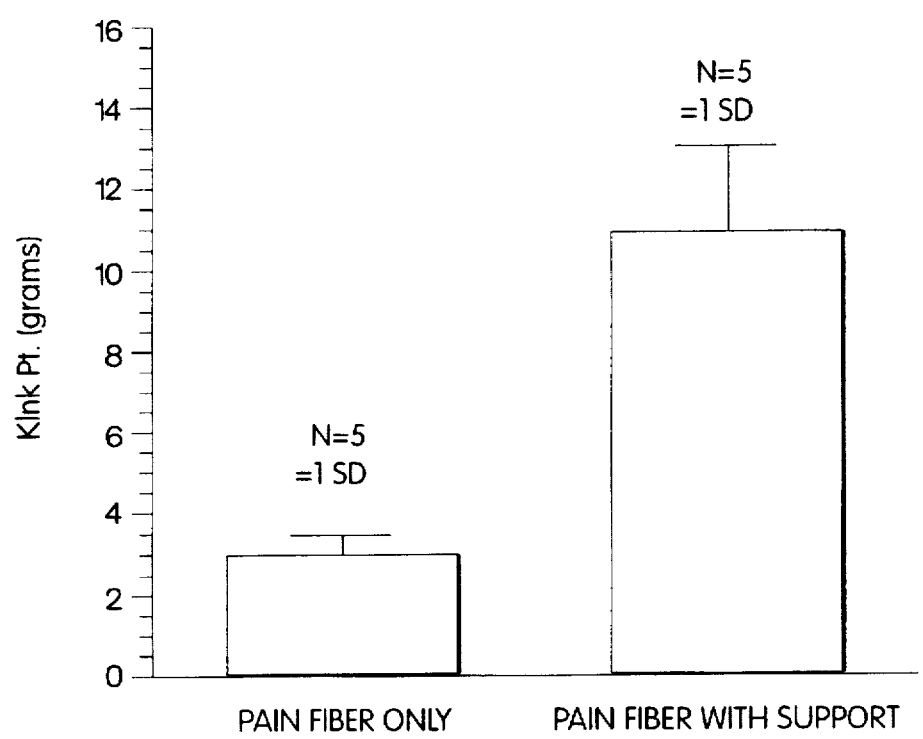
FIG. 9 is a graph comparing the weight required to kink (kink point) an inner-supported capsule and a non-inner-supported capsule.

A three point tester was used to compare stress-deflection strength of inner-supported capsules with that of non-inner-supported capsules. As shown in FIG. 9, a greater weight was required to kink inner-supported capsules than non-inner-supported capsules.

The capsules without any inner support were constructed using a double-skinned membrane cast from a dope of 12½% (w/w) PAN/PVC in DMSO, having a typical outside diameter of 900 microns and an inside diameter of 750 microns, as described in Example 1. It was sealed at both ends with a silicon sealant. The capsule length was 5 cm.

Inner-supported capsules of the same length were made by inserting a polyurethane inner support with an outside diameter of 500 microns into a hollow fiber such that an excess of inner support protruded from the distal end of the fiber and the proximal end of the fiber, also as described in Example 1. The inner support was sealed at the distal end and proximal end of the fiber with the silicon sealant. The excess inner support was then removed. No cells were added.

Example 9—Flat Sheet Inner-Supported Capsule

Flat sheet inner-supported capsules were constructed by using two circular layers of flat sheet PAN/PVC membranes (fabricated substantially according to the method of Mulder, "Basic Principle of Membrane Technology," Kluwer (1991)), to surround an inner layer of Nitex™ (a commercially available nylon screening monofilament; Tetro, Inc., Elsmford, N.Y.). The Nitex screen forms the inner support. Such a flat sheet inner supported device is illustrated in FIG. 1K. The PAN/PVC sheets and Nitex are placed into a circular mold. Polyurethane adhesive (Biothane™, Car Chem Inc.) is poured into the mold to form a polyurethane sealing ring (82) around the perimeter of the capsule. The sealing ring (82) seals the two external PAN/PVC membranes, and secures the inner support thereto. In addition, the sealing ring 82 seals silicone tubes 80, into the capsule. Silicon tubes 80 comprise access ports extending through the sealing ring to permit cell loading into the capsule. The capsule also has 3 tabs (81) for suturing the capsule in place.

Islet cell aggregates were loaded into 3 flat sheet devices through access ports (80). These devices were tested for biocompatibility and for viability of the encapsulated tissue by implantation in a 25 kg dog.

Example 10—Capsule Having Threaded Inner Support

Two centimeter sections of hollow fiber (produced by a wet/dry jet spinning technique, as described in Example 1), with a 3 mm inside diameter and 100 micron wall were cut. A six inch long threaded rod with a 1.5 mm outer diameter (Small Parts Inc.) had a small amount of silicone mold release (Dow Corning) placed on 2 cm of threads at one end of the rod. This end was then carefully slid through the hollow fiber until a small amount of the rod was protruding from the distal end. A drop of a two component polyurethane (Cas Chem Inc.) was placed over the portion of the rod that was protruding from the distal end of the hollow fiber. This secured the rod to the fiber. A drop of urethane was then placed onto the proximal end of the rod and the proximal end of the hollow fiber. This sealed and attached the rod to the hollow fiber. After the polyurethane had dried, the mold release placed on the rod allowed the rod to be gently unscrewed and removed from the hollow fiber leaving threaded polyurethane plugs at each end.

Example 11—Capsule Having End Fitting Adapted To Receive An Inner Support

A fitting having a slot adapted to receive an inner support was used in this embodiment. Such a fitting is illustrated in FIGS. 1F and 1L. The slot is on the outer rim of the fitting so that access to the central filling port is essentially unaffected by the inner support. The devices are fabricated as follows:

The inner support used in this embodiment is a titanium rod having a titanium ball welded on both ends (Star Guide Corp, Denver, Colo. 0.004"×492" Titanium rod, with 0.006" ball, for a device having a useful fiber region of approximately 1 cm.)

The slotted fitting was mounted in a holding jig so that the slot (49) could be plainly viewed. One end of the titanium rod (30) was fitted into slot 49 and a drop of LCM23 Luxtrak (Ablestick Adhesives, Zeneca Inc., Wilmington, Del.) light curable glue was applied to the rod near the ball using a syringe. When the drop filled slot 49, the glue was cured by exposure to blue light for approximately 40 seconds.

A length of hollow fiber membrane was inspected to make sure it was relatively straight and that the lumen was open. One end of the fiber (the proximal end) was slid over the rod and the bottom of the fitting (23). A drop of LCM23 was placed on the fitting 23 and the fiber drawn up with a twisting motion to distribute the glue around the circumference of the fiber). The glue was cured by exposure to blue light for 40 seconds. An additional drop of glue was placed over the fiber/slotted fitting/rod interface and smoothed out using the tip of the syringe. The glue was exposed to blue light for 40 seconds.

The distal end of the device (21) was sealed by cutting the fiber off close to the end of the titanium rod. A drop of glue was applied to the tip to form a glue seal (22). The drop was allowed to wick into the membrane slightly and was light-cured for 40 seconds. A second drop of glue was applied to the distal tip and light-cured for 40 seconds.

What is claimed is:

1. A biocompatible cell capsule for implantation, comprising:
   (a) a capsule jacket connected to a chamber top at one end and a chamber bottom at the other end enclosing a cell chamber
   (b) the capsule jacket comprising at least one semipermeable surface across which biologically active molecules can be delivered, and
   (c) an inner support having two ends extending through the cell chamber such that one end is connected to the chamber top and the other end is connected to the chamber bottom, said inner support having a tensile strength to provide an increase in tensile strength to the capsule of at least about 350% greater than when the capsule does not contain an inner support.

2. The capsule of claim 1 wherein the cell chamber top comprises a top sealing fitting and the cell chamber bottom comprises a bottom sealing fitting.

3. The capsule of claim 2 wherein the chamber has a longitudinal axis running from the center of the top sealing fitting and the center of the bottom sealing fitting and wherein the inner support is cylindrical and arranged concentrically with the longitudinal axis.

4. The capsule of claim 1 wherein the inner support is coated with a cell-adhesive substance or a cell-viability-enhancing substance.

5. The capsule of claim 1 wherein the outer surface of the inner support is roughened.

6. The capsule of claim 5 wherein the external features are fins.

7. The capsule of claim 1 wherein the capsule top comprises an annular fitting having a slot adapted to receive the inner support.

8. The capsule of claim 7, wherein the inner support comprises a rod having a ball at one end adapted to fit within said slot in said annular fitting.

9. The capsule of claim 1 wherein at least one end of the inner support has a shape providing greater surface area available for securing the inner support to the chamber top or chamber bottom.

10. The capsule of claim 1 further comprising a tether for retrieval.

11. The capsule of claim 10 wherein said tether is integrally formed with the inner support.

12. The capsule of claim 1 wherein the capsule is immunoisolatory.

13. The capsule of claim 1 wherein the outer surface of the inner support is irregularly shaped.

* * * * *